US009050222B2

(12) United States Patent
Schoenbeck

(10) Patent No.: US 9,050,222 B2
(45) Date of Patent: Jun. 9, 2015

(54) INCONTINENCE BRIEF

(75) Inventor: Marcus Schoenbeck, Versmold (DE)

(73) Assignee: MONDI GRONAU GMBH, Gronau (DE)

( * ) Notice: Subject to any disclaimer, the term of this patent is extended or adjusted under 35 U.S.C. 154(b) by 491 days.

(21) Appl. No.: 12/978,572

(22) Filed: Dec. 26, 2010

(65) Prior Publication Data

US 2011/0160690 A1 Jun. 30, 2011

(30) Foreign Application Priority Data

Dec. 29, 2009 (EP) .................... 09016074

(51) Int. Cl.
*A61F 13/64* (2006.01)
*A61F 13/62* (2006.01)
*A61F 13/49* (2006.01)
*A61F 13/56* (2006.01)

(52) U.S. Cl.
CPC ........... *A61F 13/62* (2013.01); *A61F 13/49011* (2013.01); *A61F 13/5622* (2013.01)

(58) Field of Classification Search
CPC ............. A61F 2013/4905; A61F 2013/49052; A61F 2013/49033; A61F 2013/49039; A61F 2013/49041
USPC ......... 604/353, 392, 394, 391, 395, 396, 398, 604/399, 400, 401, 402
See application file for complete search history.

(56) References Cited

U.S. PATENT DOCUMENTS

| 5,496,429 | A | * | 3/1996 | Hasse et al. .................. 156/73.3 |
| 5,620,780 | A | * | 4/1997 | Krueger et al. ............... 428/179 |
| 7,544,628 | B2 | | 6/2009 | Stupperich |
| 2007/0299418 | A1 | * | 12/2007 | Vartiainen ..................... 604/392 |
| 2010/0217218 | A1 | | 8/2010 | Baeck |

* cited by examiner

*Primary Examiner* — Tan-Uyen (Jackie) T Ho
*Assistant Examiner* — Peter S Vasat
(74) *Attorney, Agent, or Firm* — Andrew Wilford

(57) ABSTRACT

An incontinence brief for an adult wearer has an absorbent body having a fluid-permeable inner side, a fluid-tight outer side, and an absorbent liner therebetween. The body is subdivided into a central part adapted to fit in a crotch region of the wearer, a rear part connected to the central part and adapted to fit against a rear waist region of the wearer, and a front part adapted to fit against a front waist region of the wearer. Two fastening straps adapted to fit around respective sides of a waist of the wearer each have a rear end secured to the rear part and a front part. At least one of the fasteners is provided between its respective front and rear ends with an elastic layer forming an elastically stretchable region, and each of the fasteners has an outer layer formed by a water-jet consolidated fleece.

10 Claims, 3 Drawing Sheets

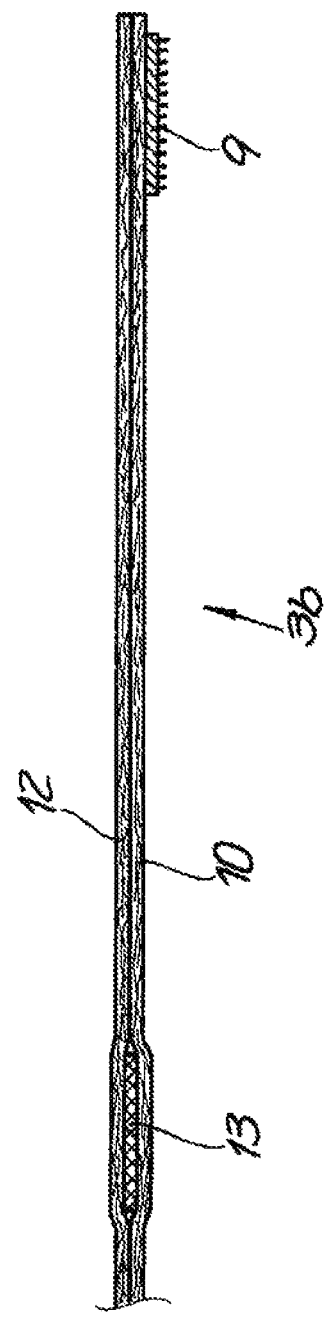

INCONTINENCE BRIEF

FIELD OF THE INVENTION

The present invention relates to an incontinence product. More particularly this invention concerns an incontinence brief for an adult.

BACKGROUND OF THE INVENTION

A standard incontinence brief such as described in DE 10 2004 053 469 A1 [U.S. Pat. No. 7,544,628] and in WO 2007/149016 has an absorbent body or pad with an inner side having or formed by a fluid-permeable inner layer, an outer side having or formed by a fluid-tight outer layer and an absorbent liner provided between the inner layer and the outer layer. This body has a central part formed to fit in the crotch region of the user, a back part rising up from the central part at a rear waist region and a front part rising up from the central part at a front waist region. Here, the terms "inner" and "outer" are relative to the body of the user of the product, the "inner" side normally lying directly against the user's body and the "outer" side being turned outward away from the user's body.

A belt assembly formed by two fastening straps holds the body or pad in place. Each strap has a rear end attached to an upper end of the back part, extends around a respective side of the wearer's waist, and has a front end that can be secured to the front end of the other fastener by a hook and barb fastener. The upper end of the front part of the body or pad and is similarly secured to an outer face of the fasteners in the front waist region. The fasteners have an outer layer made of a water-jet consolidated fleece fabric so that hook patches can be secured to them at any location.

In this arrangement the fastening straps are stiff. The belt's elasticity is created by incorporating an elastic film in the body. The manufacture of the body is therefore complex. In addition, to provide a good connection with hook-and-loop-type hooks, the fleece fabric has island-like regions that are delimited by bound, i.e. reinforced, structures. Thermoembossing, specifically calendar embossing, or ultrasonic welding is disclosed for the reinforcement. This means that in the bound regions the fibers of the fleece fabric are melted into each other, which results is a stiffening of the material, causing it to lose its elasticity. Aside from the only island-like unbound regions, the bound contours extend over the total region of the fleece material, so that a band that is cut off longitudinally that is of high tensile strength and stiffness.

Unlike baby diapers, with incontinence products for adults it is especially desirable that, in as far as possible, these products are not visible, and in particular do not leave a visible imprint through clothing. Normally, their cut is therefore different than that of baby diapers, having the absorbent pad for the most part in the crotch region with the front and back parts maintained as flat as possible. While baby diapers often have diapers wings that hug the hips of the diaper wearer at the side, where they are fastened together, the incontinence brief for adults only envisions a comparatively narrow belt for support.

Differences can also be seen in the way a baby diaper is put on in contrast to an incontinence brief for adults. For example, baby diapers are usually put on while the baby is supine. First the back waist region of the diaper is placed underneath the baby's body and the front waist region is placed on top of the stomach region. Then the side diaper wings are fastened each other on the sides of the infant. Even if the baby moves during changing, it is still comparatively easy to lift and hold him or her.

Incontinence products for adults, on the other hand are supposed to be put on, in as much as possible, while lying, sitting or even standing. An added problem is that the adult incontinence product is to be placed on the wearer by the user himself/herself or by a care giver. In addition, due to the greater weight of the user, it is especially important that the product be easy to handle. Correspondingly therefore a continuous belt is provided that supports the incontinence guard and is made up of the above-described fastening straps that extend laterally from the body so that the overall incontinence product can no longer become completely detached, even if the user is standing or moving while putting on the incontinence product. Subsequently, the front waist region is folded upward until the hook patches of the fastener can be fixed in place on the outer layer of the fastening straps like a hook-and-loop fastener.

Furthermore, also to be considered is the fact that incontinence briefs for adults should be adjustable to different body proportions. Providing incontinence products of this kind in different sizes is, not unlike baby diapers, a complex undertaking. In practical applications different products are distinguished often only by their respective absorbencies.

OBJECTS OF THE INVENTION

It is therefore an object of the present invention to provide an improved incontinence brief.

Another object is the provision of such an improved incontinence brief that overcomes the above-given disadvantages, in particular that will be cost-effective to produce while still providing great security against inadvertent opening.

SUMMARY OF THE INVENTION

An incontinence brief for an adult wearer has according to the invention an absorbent body having a fluid-permeable inner side, a fluid-tight outer side, and an absorbent liner between the inner side and the outer side. The body is subdivided into a central part adapted to fit in a crotch region of the wearer, a rear part connected to the central part and adapted to fit against a rear waist region of the wearer, and a front part adapted to fit against a front waist region of the wearer. Two fastening straps adapted to fit around respective sides of a waist of the wearer each have a rear end secured to the rear part and a front part. At least one of the fasteners is provided between its respective front and rear ends with an elastic layer forming an elastically stretchable region, and each of the fasteners has an outer layer formed by a water-jet consolidated fleece. A hook-and-barb fastener releasably secures the front ends of the straps together at the front waist region. Respective hook patches on the front part releasably secure it to the outer layers of the fastening straps at the front waist region.

The elastic layer, which is usually a film of a thickness of between 40 and 150 µm, provides for an elastic return after stretching has occurred. To achieve sufficient elasticity overall and therefore better wearer comfort, an elastic region is provided in each of the two fastening straps.

The water-jet consolidated fleece fabric is also referred to as a spunlace nonwoven fabric. The water-jet consolidation creates a loop-type fiber structure that contributes to better material stability. Surprisingly, it has been found that water-jet consolidated fleece fabric can be very easily fastened by hook patches despite the consolidation, so that a reliable hook-and-loop closure system is provided. In addition, spunbond fleece fabrics are recognizable by their cell-shaped pattern configuration featuring regions of high fiber density and low fiber density. As emphasized further below, the water-jet consolidated fleece fabric is also characterized by a certain amount of stretchability, which is especially advantageous for providing elastic regions.

The fastening straps according to the invention are formed either as the ends of a continuous fastening band or as pieces that are separate of each other and attached laterally to the body, and, correspondingly, the belt supporting the incontinence guard is constituted by the two fastening pieces and the rear waist region located between them. Irrespective of whether the fastening straps are envisioned as separate pieces or as the ends of a continuous band, the elastic region can be provided in the rear waist region and/or on at least in one of the two fastening straps.

The elastic layer is preferably hidden between the previously described outer layer that is manufactured of water-jet consolidated fleece fabric and an inner layer manufactured of fleece fabric, with this latter layer lying against the body of the wearer when the incontinence guard is in place on the wearer's body. The inner layer can be made of a different fleece than the outer layer. But special advantages are realized if the inner layer is made of a water-jet consolidated fleece fabric as well, and both the inner and outer layers are stretchable. If no further intermediate layers are envisioned aside from the only section-wise provided elastic layer between them, there results the advantage that the thereby achieved material that is in part double-layered and in part triple-layered in the fastening strap(s) is stretchable without any need for further pretreatment and elastically stretchable in the elastic regions. Therefore, during manufacture of the fastening strap, it is not necessary to apply the fleece fabric layers that are located on the outside to an elastic layer that is subject to tensile stress (stretch bond method) or to subject the thus-formed material to activation by a prestretching process. At least before first use of the incontinence product it is thus possible that the outer layer and the inner layer are lying flat and without bulging against the elastic layer. If both the inner and the outer layers are comprised of spunlace nonwoven material and excessive, nonelastic stretching is to be avoided during use it is possible to hide a stiff layer outside the elastic regions between the outer layer and the inner layer.

If in an alternative embodiment according to the invention a nonstretch fleece material is used for the inner layer, preferably the elastic regions are activated by prestretching before establishing the connection of the fastening straps with the body.

The weight per unit of area of the outer layer is preferably between 20 and 100 g/m². If an inner layer is envisioned, as has been described previously by way of a preferred embodiment, the weight per unit of area is, depending on the type of the material of the fleece fabric, between 15 and 100 g/m². In the context of the invention, an elastic film of a thickness of 40 µm and 150 µm is preferably envisioned as an elastic layer. According to the invention, with regard to its function, the film is viewed in the first place only as an elastic layer. But this is not a limitation with regard to the exact configuration of the film. Aside from a mono-film, laminates and co-extrusion films comprising several film layers are also possible.

The fastening straps are preferably made as simple straight bands and can therefore be cut off in a simple manner in a transverse direction from the material stock. As described previously, the fastening straps, intended to form a belt, are to ensure a secure hold and high wearer comfort, and moreover the fastening straps should in as much as possible not be visible under the wearer's clothing. Suitable are, for example, fastening straps that are made as straight bands of a width of between 50 mm and 150 mm. When not stretched, the length of the fastening straps is preferably at least 200 mm. But the length can, for example, also be between 250 mm and 400 mm. To be taken into account in this context is the fact that the goal is to also allow for adjustability to different body proportions.

When putting on the incontinence product, the body is first applied to the wearer by its rear waist region; then the two fastening straps are placed around the wearer thereby creating a belt, and the ends are then connected with each other. To this end, preferably at least one of the two fastening straps features an affixed hook patch on its inner layer that can be attached to the outer layer of the other fastening strap thereby forming a hook-and-loop closure. By providing for a variable overlap of the fastening straps, it is possible to adjust the belt to different body circumferences as well as the force that the belt exerts. It is preferred that the fastening straps each have, relative to the lateral edge of the body and when not under tension, a length of at least 200 mm. The length can, for example, be between 250 mm and 400 mm.

The hook patches of the hook-and-loop closure that are fastened in the front waist region of the body are preferably on the inner side of the body. In the alternative, it is also possible to envision fastening on the outer side, and in this instance the hook patches overlap the front waist region laterally or at the front edge.

The hook-and-loop closure system that is constituted by the outer layer of the spunlace nonwoven material and the associated hook patches is characterized by its high and even hook-and-loop fastening effect. This applies relative to the forces that are generated by the pull-off of the hook patches from the outer layer (peel test) as well as regarding forces that act parallel relative to the contact surface (shear test). Finally, there exists the advantage that spunlace nonwoven materials that are stretchable to a certain degree can also be manufactured at low cost.

BRIEF DESCRIPTION OF THE DRAWING

The above and other objects, features, and advantages will become more readily apparent from the following description, reference being made to the accompanying drawing in which:

FIG. 2 shown the incontinence product according to FIG. 1 while putting it on;

FIG. 3 is a section along the line in FIG. 1.

SPECIFIC DESCRIPTION

Figure 1:
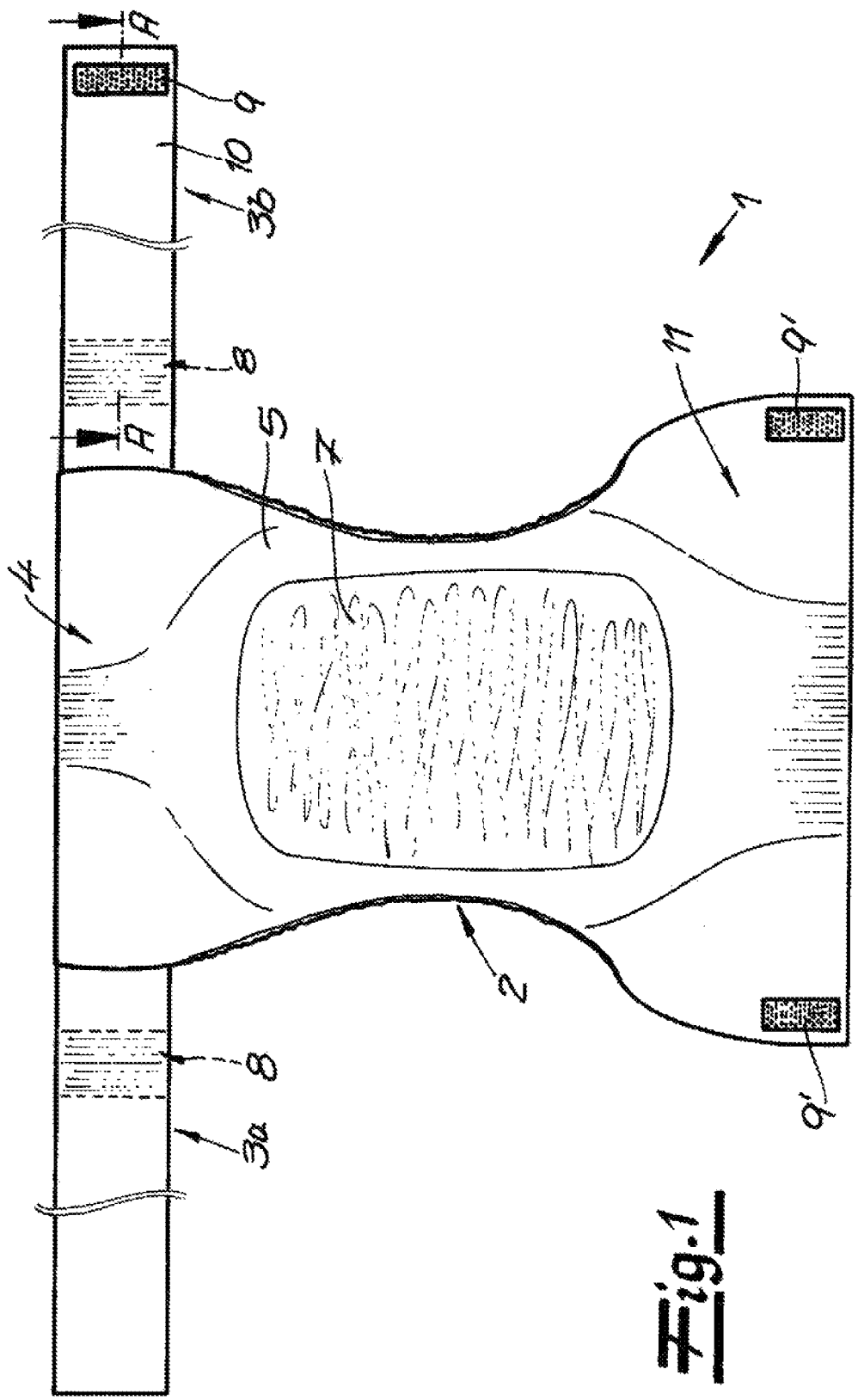
FIG. 1 is a top view of an incontinence product according to the invention in flattened-out condition prior to use.

An incontinence brief 1 according to the invention comprises an absorbent pad or body 2 and fastening straps 3*a* and 3*b* that extend starting at a rear waist part 4 of the body 2 laterally away from the body 2. This body 2 has a fluid-permeable inner layer or side 5 a fluid-tight outer layer or side 6, and an absorbent liner 7 between the inner layer 5 and the outer layer 6.

The fastening straps 3*a* and 3*b* are separate pieces. But, in the alternative, the fastening straps 3*a* and 3*b* can also be the ends of a continuous fastening band. In addition, the fastening straps 3*a* and 3*b* each have an elastic region 8. In addition, a hook patch 9 is provided on an inner layer 10 of the fastening strap 3b. Additional hook patches 9' are located in a front waist part 11 of the body 2 on the inner side of this front waist part 11.

Figure 2:
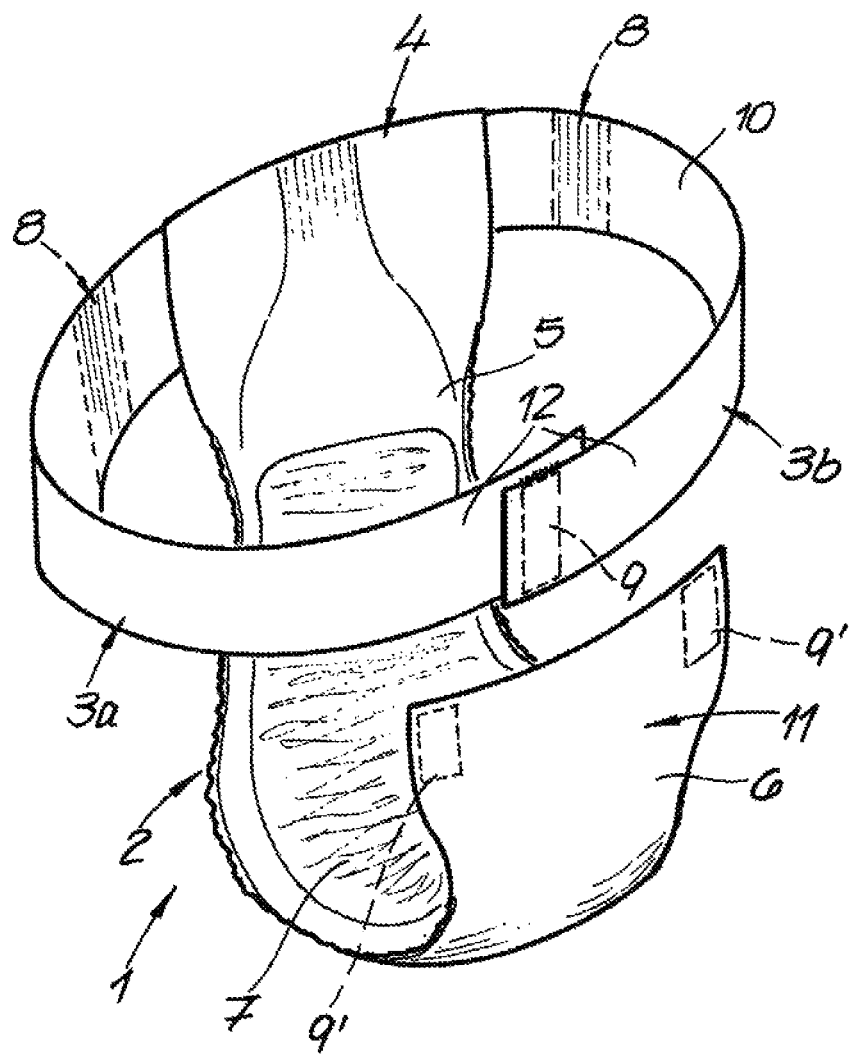

FIG. 2 shows how the incontinence brief 1 is to be placed on the wearer, and for clarity of view the actual person of the wearer has been omitted. First, the rear waist part 4 is placed on the wearer and the fastening straps 3a and 3b are placed around the wearer's waist in such a way that the hooks of the patch 9 on the inner layer 10 of the fastening strap 3b come to lie on an outer layer 12 of the other fastening strap 3a, the hook patch 9 forming a hook-and-loop closure system with the associated outer layer 12. The fastening straps 3a and 3b and the rear part 4 that is between them form a continuous belt that supports the incontinence brief 1. The front waist region 11 must then only be placed between the legs of the wearer and fastened by the hook patches 9' to the outer layers 12 of the fastening straps 3a and 3b. The resulting advantage is that the incontinence brief 1 can be easily put on while the wearer is lying, standing or sitting. The main portion of the absorbent liner 7 is in the crotch region, which means the incontinence brief 1 is only minimally visible through clothing.

Since the two fastening straps 3a and 3b can be placed on top of each other with different overlaps, it is possible to adjust the belt they form to accommodate different waist sizes and to adjust the tension that is applied in the elastic regions 8 so that a secure and comfortable fit can be achieved.

FIG. 3 shows a section of the configuration that comprises the fastening strap 3b with the hook patch 9, the other fastening strap 3a being identically made but lacking the hook patch 9. According to the invention the outer layer 12 of the fastening straps 3a and 3b is comprised of a water-jet consolidated fleece fabric, which is also referred to as spunlace nonwoven fabric. Surprisingly, the outer layer 12 that is made in this way has a very good ability to attach itself to the hook patches 9 and 9' as in a hook-and-loop closure.

In the illustrated embodiment, an elastic film 13 having typically a thickness of between 40 and 150 μm is wholly concealed in the elastic region 8 between the inner layer 10 and the outer layer 12. Furthermore, according to the shown preferred embodiment the inner layer 10 is also constituted of a water-jet consolidated fleece fabric. Since a spunlace nonwoven material of this kind, with a weight per unit of area of between 20 and 100 g/m$^2$, has a certain amount of stretchability, before the first use of the incontinence brief 1, complex activation by prestretching etc. is not necessary. Rather, the incontinence brief 1 can be made in such a way that, at least before the first use, the outer layer 12, and in the shown embodiment the envisioned inner layer 10 as well, lie flat and without bulging against the elastic film 13.

The fastening straps 3a and 3b are straight bands having a length of more than 200 mm and a width of between 50 and 150 mm.

I claim:

1. An incontinence brief for an adult wearer, the brief comprising:
    an absorbent body having a fluid-permeable inner side, a fluid-tight outer side, and an absorbent liner between the inner side and the outer side, the body being subdivided into a central part adapted to fit in a crotch region of the wearer, a rear part connected to the central part and adapted to fit against a rear waist region of the wearer, and a front part adapted to fit against a front waist region of the wearer;
    two fastening straps each having a length of at least 200 mm when not tensioned and each adapted to fit around a respective side of a waist of the wearer, each having an outer layer formed by a stretchable fleece formed of water-jet consolidated fibers, and each having a rear end secured to the rear part and a front end, one of the straps also having an inner layer provided between its respective front and rear ends and an elastic layer sandwiched in only one section between the inner and outer layers and forming an elastically stretchable region in only the one section of the one strap such that the one strap is elastically stretchable, has three layers, and is of greater thickness in the one section having the elastic layer than elsewhere, the inner and outer layers lying flat without bulges against the elastic layer in the one section, the one strap being of two layers and stretchable except at the one section;
    a hook-and-barb fastener that can releasably secure the front ends of the straps together at the front waist region; and
    respective hook patches on the front part releasably securable to the outer layers of the fastening straps at the front waist region.

2. The incontinence brief defined in claim 1, wherein the elastic layer at the one section is wholly contained between the respective inner and outer layers.

3. The incontinence brief defined in claim 1, wherein the inner layer is made of a fleece formed by water-jet consolidated fibers.

4. The incontinence brief defined in claim 1, wherein the inner layer has a weight per unit of area of between 15 g/m$^2$ and 100 g/m$^2$.

5. The incontinence brief defined in claim 1, wherein the elastic layer is a film having a thickness of between 40 μm and 150 μm.

6. The incontinence brief defined in claim 1, wherein the outer layer has a weight per unit of area of between 20 g/m$^2$ and 100 g/m$^2$.

7. The incontinence brief defined in claim 1, wherein the fastening straps are straight bands.

8. The incontinence brief defined in claim 7, wherein the fastening straps have a width of between 50 mm and 150 mm.

9. The incontinence brief defined in claim 1, wherein the hook patches are provided at the front waist region on the inner side of the body.

10. The incontinence brief defined in claim 9, wherein the elastic layer and inner and outer layers of the one strap lie flatly against each other, the elastic layer being activated by prestretching.

* * * * *